United States Patent [19]

Okamoto et al.

[11] 4,258,192

[45] * Mar. 24, 1981

[54] $N^2$-ARYLSULFONYL-L-ARGININAMIDES AND THE PHARMACEUTICALLY ACCEPTABLE SALTS THEREOF

[75] Inventors: Shosuke Okamoto, 15-18, Asahigaoka 3-chome, Tarumi-ku, Kobe-shi, Hyogo, Japan; Akiko Hijikata, Kobe, Japan; Ryoji Kikumoto; Yoshikuni Tamao, both of Machida, Japan; Kazuo Ohkubo, Komae, Japan; Tohru Tezuka, Yokohama, Japan; Shinji Tonomura, Machida, Japan

[73] Assignees: Mitsubishi Chemical Industries Limited, Tokyo; Shosuke Okamoto, Kobe, both of Japan

[ * ] Notice: The portion of the term of this patent subsequent to Sep. 19, 1995, has been disclaimed.

[21] Appl. No.: 41,419

[22] Filed: May 22, 1979

Related U.S. Application Data

[60] Continuation-in-part of Ser. No. 938,711, Aug. 31, 1978, which is a continuation-in-part of Ser. No. 844,188, Oct. 21, 1977, Pat. No. 4,117,127, which is a division of Ser. No. 760,745, Jan. 19, 1977, Pat. No. 4,066,773, which is a continuation-in-part of Ser. No. 653,217, Jan. 28, 1976, Pat. No. 4,055,651, Ser. No. 713,486, Aug. 11, 1976, Pat. No. 4,073,914, Ser. No. 703,704, Jul. 8, 1976, Pat. No. 4,069,323, and Ser. No. 671,436, Mar. 29, 1976, Pat. No. 4,066,758, which is a division of Ser. No. 622,390, Oct. 14, 1975, abandoned.

[30] Foreign Application Priority Data

Dec. 16, 1977 [CA] Canada .................................. 293199

[51] Int. Cl.$^3$ ..................... A61K 31/47; C07D 215/36
[52] U.S. Cl. ..................................... 546/166; 424/258
[58] Field of Search ................................ 546/172, 166

[56] References Cited

U.S. PATENT DOCUMENTS

| | | | |
|---|---|---|---|
| 4,066,773 | 1/1977 | Okamoto et al. | 424/267 |
| 4,069,329 | 1/1978 | Okamoto et al. | 424/267 |
| 4,117,127 | 9/1978 | Okamoto et al. | 424/247 |
| 4,125,604 | 11/1978 | Okamoto et al. | 424/177 |
| 4,131,673 | 12/1978 | Okamoto et al. | 424/247 |

*Primary Examiner*—Donald G. Daus
*Assistant Examiner*—Diana G. Rivers
*Attorney, Agent, or Firm*—Oblon, Fisher, Spivak, McClelland & Maier

[57] ABSTRACT

$N^2$-Arylsulfonyl-L-argininamides and the pharmaceutically acceptable salts thereof have been found to be effective as pharmaceutical agents for the inhibition and suppression of thrombosis in mammals.

8 Claims, No Drawings

N²-ARYLSULFONYL-L-ARGININAMIDES AND THE PHARMACEUTICALLY ACCEPTABLE SALTS THEREOF

CROSS-REFERENCE TO RELATED APPLICATIONS

This application is a continuation-in-part of Ser. No. 938,711 filed Aug. 31, 1978, which in turn is a continuation-in-part of 844,188 filed Oct. 21, 1977 now U.S. Pat. No. 4,117,127 which in turn is a divisional of Ser. No. 760,745 filed Jan. 19, 1977, now U.S. Pat. No. 4,066,773, which is a continuation-in-part of the following applications:

Ser. No. 653,217 of Jan. 28, 1976, now U.S. Pat. No. 4,055,651

Ser. No. 713,486 of Aug. 11, 1976, now U.S. Pat. No. 4,073,914

Ser. No. 671,436 of Mar. 29, 1976, now U.S. Pat. No. 4,066,758

Ser. No. 703,704 of Jul. 8, 1976, now U.S. Pat No. 4,069,323

The Ser. No. 671,436 is a divisional of Ser. No. 622,390 filed Oct. 14, 1975, now abandoned.

BACKGROUND OF THE INVENTION

1. Field of the Invention

This invention relates to the discovery of certain new and useful N²-arylsulfonyl-L-argininamides and the pharmaceutically acceptable salts thereof, which are of especial value in view of their outstanding antithrombotic properties and low toxicities.

2. Description of the Prior Art

In the past, there have been many attempts to obtain new and improved agents for the treatment of thrombosis. The N²-(p-tolysulfonyl)-L-arginine esters have been found to be one type of agent which can be used and these have been found to be effective in dissolving blood clots. (U.S. Pat. No. 3,622,615, issued Nov. 23, 1971). One family of compounds which have been found to be particularly useful as highly specific inhibitors of thrombin for the control of thrombosis is the N²-dansyl-L-arginine ester or amide (U.S. Pat. No. 3,978,045) and many N²-arylsulfonyl-L-argininamides. However, there is a continuing need for a highly specific inhibitor of thrombin for the control of thrombosis, which exhibits lower toxicity.

SUMMARY OF THE INVENTION

It has now been discovered that N²-arylsulfonyl-L-argininamides having a specific configuration exhibit anti-thrombotic activity and even lower toxicity levels at the same relative potencies, as compared with the known N²-arylsulfonyl-L-argininamides.

The present invention provides an N²-arylsulfonyl-L-argininamide of the formula (I):

$$\begin{array}{c} HN \\ \diagdown \\ \phantom{H_2N}C-N-CH_2CH_2CH_2CHCOR_1 \\ \diagup \phantom{HHH} | \phantom{HHHHHHH} | \\ H_2N \phantom{HH} H \phantom{HHHHH} HNSO_2 \\ \phantom{HHHHHHHHHHHHH} | \\ \phantom{HHHHHHHHHHHHH} Ar \end{array} \quad (I)$$

wherein $R_1$ is (2R,4R)-4-alkyl-2-carboxy-1-piperidino said alkyl being $C_1$-$C_5$ alkyl; and Ar is 1,2,3,4-tetrahydro-8-quinolyl optionally substituted with at least one $C_1$-$C_3$ alkyl.

Also encompassed within this invention are pharmaceutically acceptable salts thereof.

This invention also relates to a method for inhibiting activity and suppressing activation of thrombin in vivo in mammals which comprises administering to a mammal a pharamaceutically (antithrombotically) effective amount of an N²-arylsulfonyl-L-argininamide or the pharmaceutically acceptable salts thereof.

DETAILED DESCRIPTION OF THE PREFERRED EMBODIMENTS

This invention relates to a group of N²-arylsulfonyl-L-argininamides of the formula (I):

$$\begin{array}{c} HN \\ \diagdown \\ \phantom{H_2N}C-N-CH_2CH_2CH_2CHCOR_1 \\ \diagup \phantom{HHH} | \phantom{HHHHHHH} | \\ H_2N \phantom{HH} H \phantom{HHHHH} HNSO_2 \\ \phantom{HHHHHHHHHHHHH} | \\ \phantom{HHHHHHHHHHHHH} Ar \end{array} \quad (I)$$

wherein $R_1$ is (2R,4R)-4-alkyl-2-carboxy-1-piperidino, said alkyl containing 1-5 (preferably 1-3) carbon atoms; and Ar is 1,2,3,4-tetrahydro-8-quinolyl optionally substituted with at least one (preferably one or two) alkyl of 1-3 (preferably 1-2) carbon atoms, and the preferred Ar is 3-alkyl-1,2,3,4-tetrahydro-8-quinolyl, said alkyl containing 1-3 (preferably 1-2) carbon atoms.

Typical compounds of this invention include:

(2R,4R)-1-[N²-(1,2,3,4-tetrahydro-8-quinolinesulfonyl)-L-arginyl]-4-methyl-2-piperidinecarboxylic acid (2R,4R)-1-[N²-(1,2,3,4-tetrahydro-8-quinolinesulfonyl)-L-arginyl]-4-ethyl-2-piperidinecarboxylic acid (2R,4R)-1-[N²-(3-methyl-1,2,3,4-tetrahydro-8-quinolinesulfonyl)-L-arginyl]-4-methyl-2-piperidinecarboxylic acid (2R,4R)-1-[N²-(3-methyl-1,2,3,4-tetrahydro-8-quinolinesulfonyl)-L-arginyl]-4-ethyl-2-piperidinecarboxylic acid (2R,4R)-1-[N²-(3-ethyl-1,2,3,4-tetrahydro-8-quinolinesulfonyl)-L-arginyl]-4-methyl-2-piperidinecarboxylic acid (2R,4R)-1-[N²-(3-ethyl-1,2,3,4-tetrahydro-8-quinolinesulfonyl)-L-arginyl]-4-ethyl-2-piperidinecarboxylic acid The pharmaceutically acceptable salts of the above compounds are of course also included within the scope of this invention.

For the preparation of the compounds of this invention, various methods can be employed depending upon the particular starting materials and/or intermediates involved. Successful preparation of these compounds is possible by way of a synthetic route which is outlined below.

$$\begin{array}{c} HN \\ \diagdown \\ \phantom{H_2N}C-N-CH_2CH_2CH_2CHCOOH \\ \diagup \phantom{HHH} | \phantom{HHHHHHH} | \\ H_2N \phantom{HH} H \phantom{HHHHH} NH_2 \end{array} \quad (II) \longrightarrow$$

$$\begin{array}{c} HN \\ \diagdown \\ \phantom{HH}C-N-CH_2CH_2CH_2CHCOOH \\ \diagup \phantom{HHH} | \phantom{HHHHHHH} | \\ HN \phantom{HHH} R'' \phantom{HHHHH} HN \\ | \phantom{HHHHHHHHHHHHHHH} | \\ R' \phantom{HHHHHHHHHHHHHHH} R''' \end{array} \quad (III) +$$

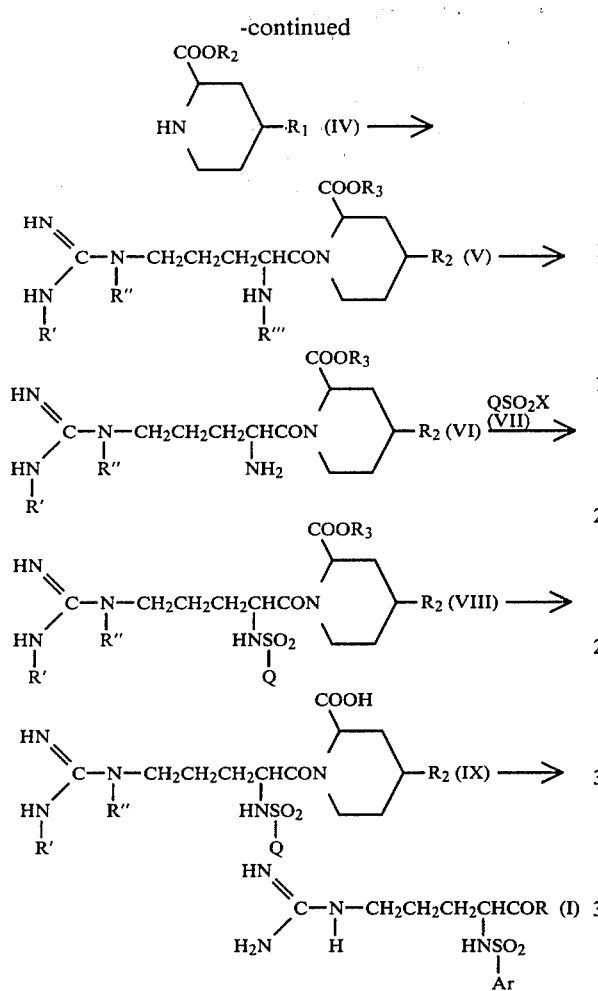

In the above formulas, $R_1$ is (2R,4R)-4-alkyl-2-carboxypiperidino which is represented for convenience of illustration by the formula

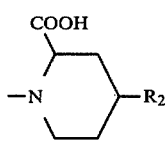

wherein $R_2$ is $C_1$-$C_5$ alkyl; Ar is as defined herein above; X is halogen; R''' is a protective group for the α-amino group, such as benzyloxycarbonyl or tert-butoxycarbonyl; R' and R'' are selected from the group consisting of hydrogen and protective groups for the guanidino group, such as nitro, tosyl, trityl, oxycarbonyl and the like; and at least one of R' and R'' is a protective group for the guanidino group; $R_3$ is lower alkyl such as methyl and ethyl; and Q is 8-quinolyl optionally substituted with at least one $C_1$-$C_3$ alkyl, which is corresponding to Ar.

The $N^2$-arylsulfonyl-L-argininamide (I) is prepared by removing the $N^G$-substituent from an $N^G$-substituted-$N^2$-quinolylsulfonyl-L-argininamide (IX) by means of hydrogenolysis and, at the same time, hydrogenating the quinolyl moiety to the corresponding 1,2,3,4-tetrahydroquinolyl moiety.

The removal of the nitro group and the oxycarbonyl group, e.g., benzyloxycarbonyl, p-nitrobenzyloxycarbonyl, is readily accomplished by the hydrogenolysis.

The hydrogenolysis and hydrogenation are effected in a reaction-inert solvent, e.g., methanol, ethanol, tetrahydrofuran or dioxane, in the presence of a hydrogen-activating catalyst, e.g., Raney nickel, palladium, or platinum, ruthenium, rhodium, in a hydrogen atmosphere at a temperature of 0° C. to 200° C. and preferably 50° C. to 150° C. for a period of 2 hours to 120 hours.

In general, the hydrogen pressure is in the range of 1 to 100 kg/cm², and preferably in the range of 5 to 50 kg/cm². It is necessary to continue the hydrogenolysis and hydrogenation until a stoichiometric amount of hydrogen is absorbed.

The $N^2$-arylsulfonyl-L-argininamides (I) are isolated by filtration of the catalyst followed by evaporation of the solvent, and then purified by trituration or recrystallization from a suitable solvent, such as diethyl ether-tetrahydrofuran, diethyl ether-methanol and water-methanol, or may be chromatographed on silica gel or alumina.

(2R,4R)-1-($N^G$-substituted-$N^2$-quinolylsulfonyl-L-arginyl)-2-piperidinecarboxylic acids (IX) can be prepared by hydrolyzing an alkyl (2R,4R)-1-($N^G$-substituted-$N^2$-quinolylsulfonyl-L-arginyl)-2-piperidinecarboxylate (VIII) by a conventional procedure well known in the art.

The alkyl (2R,4R)-1-($N^G$-substituted-$N^2$-quinolylsulfonyl-L-arginyl)-2-piperidinecarboxylate (VIII) can be prepared by condensing an $N^G$-substituted-$N^2$-substituted L-arginine (III) (generally the $N^G$-substituent is nitro or acyl, and the $N^2$-substituent is a protective group for the amino group, such as benzyloxycarbonyl, tert-butoxycarbonyl, or the like) and an alkyl (2R,4R)-4-alkyl-2-piperidinecarboxylate (IV), selectively removing only the $N^2$-substituent of an $N^G$-substituted-$N^2$-substituted L-argininamide (V) by means of catalytic hydrogenolysis or acidolysis, and then condensing the thus obtained $N^G$-substituted-L-argininamide (VI) with a quinolinesulfonyl halide (VII), preferably a chloride in the presence of a base in a solvent.

The $N^2$-arylsulfonyl-L-argininamide (I) of this invention forms acid addition salts with any of a variety of inorganic and organic acids. They also form salts with any of a variety of inorganic and organic bases.

The product of the reactions described above can be isolated in the free form or in the form of salts. In addition, the product can be obtained as pharmaceutically acceptable acid addition salts by reacting one of the free bases with an acid, such as hydrochloric, hydrobromic, hydroiodic, nitric, sulfuric, phosphoric, acetic, citric, maleic, succinic, lactic, tartaric, gluconic, benzoic, methanesulfonic, ethanesulfonic, benzenesulfonic, p-toluenesulfonic acid or the like. In a similar manner, the product can be obtained as pharmaceutically acceptable salts by reacting one of the free carboxylic acids with a base, such as sodium hydroxide, potassium hydroxide, ammonium hydroxide, triethylamine, procaine, dibenzylamine, 1-ephenamine, N,N'-dibenzylethylenediamine, N-ethylpiperidine or the like.

Likewise, treatment of the salts with a base or acid results in a regeneration of the free amide.

As stated above, the $N^2$-arylsulfonyl-L-argininamides, and the salts thereof of this invention are characterized by their highly specific inhibitory activity in mammals against thrombin as well as by their substantial lack of toxicity, and therefore these compounds are useful in the determination of thrombin in blood as diagnostic reagents, and/or for the medical control or prevention of thrombosis.

The compounds of this invention are also useful as an inhibitor of platelet aggregation.

The antithrombotic activity of the $N^2$-arylsulfonyl-L-argininamide of this invention was compared with that of a known antithrombotic agent, $N^2$-(p-tolylsulfonyl)-L-arginine methyl ester, by determining the fibrinogen coagulation time. The measurement of the fibrinogen coagulation time was conducted as follows:

An 0.8 ml aliquot of a fibrinogen solution, which had been prepared by dissolving 150 mg of bovine fibrinogen (Cohn fraction I) supplied by Armour Inc. in 40 ml of a borate saline buffer (pH 7.4), was mixed with 0.1 ml of a borate saline buffer, pH 7.4, (control) or a sample solution in the same buffer, and 0.1 ml of a thrombin solution (5 units/ml) supplied by Mochida Pharmaceutical Co., Ltd. was added to the solutions in an ice bath.

Immediately after mixing, the reaction mixture was transferred from the ice bath to a bath maintained at 25° C. Coagulation times were taken as the period between the time of transference to the 25° C. bath and the time of the first appearance of fibrin threads. In the cases where no drug samples were added, the coagulation time was 50–55 seconds.

The term "concentration required to prolong the coagulation time by a factor of two" is the concentration of an active ingredient required to prolong the normal coagulation time 50–55 seconds to 100–110 seconds.

The concentration required to prolong the coagulation time by a factor of two for the known antithrombotic agent, $N^2$-(p-tolylsulfonyl)-L-arginine methyl ester, was 1,100 μm. On the other hand, the concentration required to prolong the coagulation time by a factor of two for the compound of this invention, (2R,4R)-1-$N^2$-(3-methyl-1,2,3,4-tetrahydro-8-quinolinesulfonyl)-L-arginyl-4-methyl-2-piperidinecarboxylic acid, was 0.035 μM.

When a solution containing an $N^2$-arylsulfonyl-L-argininamide of this invention was administered intravenously into animal bodies, the high antithrombotic activity in the circulating blood was maintained for from one to three hours. The halflife for decay of the anti-thrombotic compounds of this invention in circulating blood was shown to be approximately 60 minutes; the physiological conditions of the host animals (rats, rabbit, dog and chimpanzee) were well maintained. The experimental decrease of fibrinogen in animals caused by infusion of thrombin was satisfactorily controlled by simultaneous infusion of the compounds of this invention.

The acute toxicity values ($LD_{50}$) determined by intravenous administration of substances of formula (I) in mice (male, 20 g) range from about 100 to 500 milligrams per kilogram of body weight.

A representative $LD_{50}$ value for (2R,4R)-1-$N^2$-(3-methyl-1,2,3,4-tetrahydro-8-quinolinesulfonyl)-L-arginyl-4-methyl-2-piperidinecarboxylic acid is 210 milligrams per kilogram.

On the other hand, $LD_{50}$ values for $N^2$-dansyl-N-butyl-L-argininamide and $N^2$-dansyl-N-methyl-N-butyl-L-argininamide are 10 and 5 milligrams per kilogram, respectively.

The therapeutic agents in this invention may be administered to mammals, including humans, along or in combination with pharmaceutically acceptable carriers, the proportion of which is determined by the solubility and chemical nature of the compound, chosen route of administration and standard pharmaceutical practice.

For example, the compounds may be injected parenterally, that is, intramuscularly, intravenously or subcutaneously. For parenteral administration, the compounds may be used in the form of sterile solutions containing other solutes, for example, sufficient saline or glucose to make the solution isotonic. The compounds may be administered orally in the form of tablets, capsules, or granules containing suitable excipients such as starch, lactose, white sugar and the like.

The compounds may be administered sublingually in the form of troches or lozenges in which each active ingredient is mixed with sugar or corn syrups, flavoring agents and dyes, and then dehydrated sufficiently to make the mixture suitable for pressing into solid form. The compounds may be administered orally in the form of solutions which may contain coloring and flavoring agents. Physicians will determine the dosage of the present therapeutic agents which will be most suitable for humans, and dosages vary with the mode of administration and the particular compound chosen. In addition, the dosage will vary with the particular patient under treatment.

When the composition is administered orally, a larger quantity of the active agent will be required to produce the same effect as caused with a smaller quantity given parenterally.

The therapeutic dosage is generally 10–50 mg/kg of active ingredient parenterally, 10–500 mg/kg orally per day.

Having generally described the invention, a more complete understanding can be obtained by reference to certain specific examples, which are included for purposes of illustration only and are not intended to be limiting unless otherwise specified.

It is to be understood that the present invention includes pharmaceutical compositions containing a compound of the invention as an active ingredient. Such compositions may be in the forms described above. In particular, the invention includes such compositions in unit dose form.

1. Fractionation of trans and cis forms of ethyl 4-methyl-2-piperidinecarboxylate Trans and cis forms of ethyl 4-methyl-2-piperidinecarboxylate were fractionated by distillation in vacuo. Trans form; b.p. 83°–5°/7 mm Hg: Cis form; b.p. 107°–8°/5 mm Hg.

2. Optical resolution of trans form

Racemic ethyl 4-methyl-2-piperidinecarboxylate (trans form) was hydrolyzed by boiling with an excess of conc. HCl for 4 hrs. to give 4-methyl-2-piperidinecarboxylic acid HCl. A desalting of the amino acid HCl was carried out by chromatography using H form ion-exchange resin (Daiaion SK-112 manufactured by Mitsubishi Chemical Industries Limited) in usual method to give racemic 4-methyl-2-piperidinecarboxylic acid. To a solution of the racemic amino acid (143.2 g) in boiling 95% ethyl alcohol (2,900 ml) was added L-tartaric acid (150 g). Upon cooling, the precipitated salt (145.9 g) was collected by filtration. The crude crystals were recrystallized from 90% ethyl alcohol (1,000 ml) to give (2R,4R)-4-methyl-2-piperidinecarboxylic acid L-tartaric acid, m.p. 183.9°–185.0° C., $[\alpha]_D^{26} = +4.4$ (C=10 in H$_2$O), Analysis Calcd. for C$_{11}$H$_{19}$NO$_8$ (percent): C, 45.05, H, 6.53, N, 4.77 Found (percent): C, 45.12, H, 6.48, N, 4.70. The absolute configulation of the molecule was established by X-ray analysis of the crystal which is a 1:1 complex of the molecule with L-tartaric acid. The product was chromatographed on 2,000 ml of Diaion SK-112 ion-exchange resin packed in water, washed with water and eluted with 3% ammonium hydroxide solution. The fraction eluted from 4% ammonium hydroxide solution was evaporated to dryness to give (2R,4R)-4-methyl-2-piperidinecarboxylic acid (63.0 g) as powdery crystal. Recrystallization of the product from EtOH-H$_2$O yielded the corresponding amino acid, (2R,4R)-4-methyl-2-piperidinecarboxylic acid, m.p. 275.0°–277.8° C., $[\alpha]_D^{18}$ = −18.0 (C=10 2N-HCl), Analysis Calcd. for C$_7$H$_{13}$NO$_2$ (percent): C, 58.72, H, 9.15, N, 9.78 Found: C, 58.80, H, 9.09, N, 9.71.

3. Preparation of ethyl (2R,4R)-4-methyl-2-piperidinecarboxylate

Thionyl chloride (128.6 g) added dropwise to a stirred suspension of (2R,4R)-4-methyl-2-piperidinecarboxylic acid (51.6 g) in absolute ethyl alcohol (690 ml) below 30° C. and stirring continued for 1 hr. at room temperature and then for 1 hr. under reflux. After evaporation of the solvent, the residue was dissolved in benzene (500 ml), washed with 5% K$_2$CO$_3$ solution (100 ml) and saturated NaCl solution (200 ml), and dried over anhydrous Na$_2$SO$_4$. Upon evaporation of benzene, the residue was distillated in vacuo to give ethyl (2R,4R)-4-methyl-2-piperidinecarboxylate (57.4 g), b.p. 83°–5° C./7 mm Hg, $[\alpha]_D^{22}$ = −24.0 (C=5 in EtOH), Analysis Calcd. for C$_9$H$_{17}$NO$_2$ (percent): C, 63.13, H, 10.00, N, 8.18 Found (percent): C, 63.20, H, 9.96, N, 8.12.

EXAMPLE 1

(A) Ethyl (2R,4R)-1-[N$^G$-nitro-N$^2$-(tert-butoxycarbonyl)-L-arginyl]-4-methyl-2-piperidinecarboxylate To a stirred solution of 28.3 g of N$^G$-nitro-N$^2$-(tert-butoxycarbonyl)-L-arginine in 450 ml of dry tetrahydrofuran were added in turn 9.0 g of triethylamine and 12.2 g of isobutyl chloroformate while keeping the temperature at −20° C. After 10 minutes, to this was added 15.2 g of ethyl (2R,4R)-4-methyl-2-piperidinecarboxylate and the mixture was stirred for 10 minutes at −20° C. At the end of this period, the reaction mixture was warmed to room temperature. The solvent was evaporated and the residue taken up in 400 ml of ethyl acetate, and washed successively with 200 ml of water, 100 ml of 5% sodium bicarbonate solution, 100 ml of 10% citric acid solution and 200 ml of water. The ethyl acetate solution was dried over anhydrous sodium sulfate.

The solution was evaporated to give 31.3 g (74.5 percent) of ethyl (2R,4R)-1-[N$^G$-nitro-N$^2$-(tert-butoxycarbonyl)-L-arginyl]-4-methyl-2-piperidinecarboxylate in the form of a syrup.

I.R. (KBr): 3,300, 1,730, 1,680 cm$^{-1}$ (B) Ethyl (2R,4R)-1-[N$^G$-nitro-L-arginyl]-4-methyl-2-piperidinecarboxylate hydrochloride To a stirred solution of 30 g of ethyl (2R,4R)-1-[N$^G$-nitro-N$^2$-(tert-butoxycarbonyl)-L-arginyl]-4-methyl-2-piperidinecarboxylate in 50 ml of ethyl acetate was added 80 ml of 10% dry HCl-ethyl acetate at 0° C. After 3 hours, to this solution was added 200 ml of dry ethyl ether to precipitate a viscous oily product.

This was filtered and washed with dry ethyl ether to give ethyl (2R,4R)-1-[N$^G$-nitro-L-arginyl]-4-methyl-2-piperidinecarboxylate hydrochloride as an amorphous solid.

(C) Ethyl (2R,4R)-1-[N$^G$-nitro-N$^2$-(3-methyl-8-quinolinesulfonyl)-L-arginyl]-4-methyl-2-piperidinecarboxylate To a stirred solution of 25 g of ethyl (2R,4R)-1-(N$^G$-nitro-L-arginyl)-4-methyl-2-piperidinecarboxylate hydrochloride in 200 ml of chloroform were added in turn 18.5 g of triethylamine, and 14.7 g of 3-methyl-8-quinolinesulfonyl chloride at 5° C., and stirring was continued for 3 hours at room temperature. At the end of this period, the solution was washed twice with 50 ml of water.

The chloroform solution was dried over anhydrous sodium sulfate. Upon evaporation of the solvent, the residue was chromatographed on 50 g of silica gel packed in chloroform, washed with chloroform and eluted with 3% methanol-chloroform. The fraction eluted from 3% methanol-chloroform was evaporated to give 32.5 g (92.1 percent) of ethyl (2R,4R)-1-[N$^G$-nitro-N$^2$-(3methyl-8-quinolinesulfonyl)-L-arginyl]-4-methyl-2-piperidinecarboxylate in the form of an amorphous solid.

I.R. (KBr): 3,250, 1,725, 1,640 cm$^{-1}$ (D) (2R,4R)-1-[N$^G$-nitro-N$^2$-(3-methyl-8-quinolinesulfonyl)-L-arginyl]-4-methyl-2-piperidinecarboxylate acid A solution of 30 g of ethyl (2R,4R)-1-[N$^G$-nitro-N$^2$-(3-methyl-8-quinolinesulfonyl)-L-arginyl]-4-methyl-2-piperidinecarboxylate in 100 ml of ethanol and 100 ml of 1N sodium hydroxide solution was stirred for 24 hrs. at room temperature. At the end of this period, the solution was neutralized with 1N hydrochloric acid and then concentrated to 70 ml.

The solution was adjusted to pH 11 with 1N sodium hydroxide solution, washed with 100 ml of ethyl acetate, and then 100 ml of chloroform, acidified with 1N hydrochloric acid.

The resulting precipitate was filtered and washed with 20 ml of water to give 27 g (95% yield) of (2R,4R)-1-[N$^G$-nitro-N$^2$-(3-methyl-8-quinolinesulfonyl)-L-arginyl]-4-methyl-2-piperidinecarboxylic acid, m.p. 211°–213° C.

IR (KBr): 3,280, 1,720, 1,620 cm$^{-1}$

Analysis Calcd. for C$_{23}$H$_{31}$N$_7$O$_7$S (percent): C, 50.26; H, 5.69; N, 17.84. Found (percent): C, 50.05; H, 5.45; N, 17.45.

(E) (2R,4R)-1-[N$^2$-(3methyl-1,2,3,4-tetrahydro-8-quinolinesulfonyl)-L-arginyl]-4-methyl-2-piperidinecarboxylic acid To a solution of 3.00 g of 1-[N$^G$-nitro-N$^2$-(3-methyl-8-quinolinesulfonyl)-L-arginyl]-4-methyl-2-piperidinecarboxylic acid in 40 ml of ethanol and 10 ml of acetic acid was added 0.3 g of 5% palladium carbon and then the mixture was shaken under 50 kg/cm$^2$ hydrogen pressure at 80° C. for 4 hrs. At the end of this period, the solution was filtered to remove the catalyst and evaporated.

The residual viscous oil was shaken with a mixture of 30 ml of chloroform and 30 ml of saturated sodium bicarbonate solution. The chloroform layer was washed with 30 ml of water and evaporated. The resulting crude crystal was recrystallized from ethanol to give 2.6 g (94% yield) of (2R,4R)-1-[N$^2$-(3-methyl-1,2,3,4-tetrahydro-8-quinolinesulfonyl)-L-arginyl]-4methyl-2-piperidinecarboxylic acid, m.p. 188°–191° C.

IR (KBr): 3,400, 1,620, 1,460, 1,380 cm$^{-1}$

NMR: 100 MHz in CD$_3$OD δ-value; 6.5 (triplet 1H) 7.1 (doublet 1H), 7.4 (doublet 1H)

Analysis Calcd. for C$_{23}$H$_{36}$N$_6$O$_5$S (percent): C, 54.31; H, 7.13; N, 16.52. Found (percent) C, 54.05; H, 6.94; N, 16.65.

EXAMPLE 2

Tablets Suitable for Oral Administration

Tablets containing the ingredients indicated below may be prepared by conventional techniques.

| Ingredient | Amount per tablet (mg) |
|---|---|
| (2R,4R)-1-[N$^2$-(3-methyl-1,2,3,4-tetrahydro-8-quinolinesulfonyl)-L-arginyl]-4-methyl-2-piperidinecarboxylic acid | 250 |
| Lactose | 140 |
| Corn starch | 35 |
| Talcum | 20 |
| Magnesium stearate | 5 |
| Total | 450 mg |

EXAMPLE 3

Capsules for Oral Administration

Capsules of the below were made up by thoroughly mixing together batches of the ingredients and filling hard gelatin capsules with the mixture.

| Ingredient | Amount per capsule (mg) |
|---|---|
| (2R,4R)-1-[N$^2$-(3-methyl-1,2,3,4-tetrahydro-8-quinolinesulfonyl)-L-arginyl]-4-methyl-2-piperidinecarboxylic acid | 250 |
| Lactose | 250 |
| Total | 500 mg |

EXAMPLE 4

Sterile Solution for Infusion

The following ingredients are dissolved in water for intravenous perfusion and the resulting solution is then sterilized.

| Ingredients | Amount (g) |
|---|---|
| (2R,4R)-1-[N$^2$-(3-methyl-1,2,3,4-tetrahydro-8-quinolinesulfonyl)-L-arginyl]-4-methyl-2-piperidinecarboxylic acid | 25 |
| Buffer system | As desired |
| Glucose | 25 |
| Distilled water | 500 |

Having now fully described the invention, it will be apparent to one of ordinary skill in the art that many changes and modifications can be made thereto without departing from the spirit of the invention as set forth herein.

What is claimed as new and intended to be covered by Letters Patent of the United States:

1. An N$^2$-arylsulfonyl-L-argininamide of the formula (I):

$$\begin{array}{c} HN \\ \phantom{H_2N}\diagdown \\ \phantom{xx}C-N-CH_2CH_2CH_2CHCOR_1 \\ \diagup \phantom{xx} | \phantom{xxxxxxxxx} | \\ H_2N \phantom{xx} H \phantom{xxxxxx} HNSO_2 \\ \phantom{xxxxxxxxxxxxxxxxxx} | \\ \phantom{xxxxxxxxxxxxxxxxxx} Ar \end{array} \quad (I)$$

wherein R is (2R,4R)-4-alkyl-2-carboxy-1-piperidino said alkyl being C$_1$–C$_5$ alkyl; and Ar is 1,2,3,4-tetrahydro-8-quinolyl optionally substituted with at least one C$_1$–C$_3$ alkyl.

2. The compound of claim 1 wherein the alkyl group in the 4-position of the piperidine ring contains 1 to 3 carbon atoms and Ar is 3-alkyl-1,2,3,4-tetrahydro-8-quinolyl said alkyl being C$_1$-C$_3$ alkyl.

3. The compound of claim 1, which is (2R,4R)-1-[N$^2$-(1,2,3,4-tetrahydro-8-quinolinesulfonyl)-L-arginyl]-4-methyl-2-piperidinecarboxylic acid.

4. The compound of claim 1, which is (2R,4R)-1-[N$^2$-(1,2,3,4-tetrahydro-8-quinolinesulfonyl)-L-arginyl]-4-ethyl-2-piperidinecarboxylic acid.

5. The compound of claim 2, which is (2R,4R)-1-[N$^2$-(3-methyl-1,2,3,4-tetrahydro-8-quinolinesulfonyl)-L-arginyl]-4-methyl-2-piperidinecarboxylic acid.

6. The compound of claim 2, which is (2R,4R)-1-[N$^2$-(3-methyl-1,2,3,4-tetrahydro-8-quinolinesulfonyl)-L-arginyl]-4-ethyl-2-piperidinecarboxylic acid.

7. The compound of claim 2, which is (2R,4R)-1-[N$^2$-(3-ethyl-1,2,3,4-tetrahydro-8-quinolinesulfonyl)-L-arginyl]-4-methyl-2-piperidinecarboxylic acid.

8. The compound of claim 2, which is (2R,4R)-1-[N$^2$-(3-ethyl-1,2,3,4-tetrahydro-8-quinolinesulfonyl)-L-arginyl]-4ethyl-2-piperidinecarboxylic acid.

* * * * *